US012778543B2

(12) United States Patent
Beutel et al.

(10) Patent No.: US 12,778,543 B2
(45) Date of Patent: Nov. 3, 2026

(54) METHOD, A COMPUTER PROGRAM PRODUCT, AND A DEVICE FOR DETERMINING A CROSS-SECTIONAL WIDTH OF AN ARTERY

(71) Applicant: Stichting IMEC Nederland, Eindhoven (NL)

(72) Inventors: Fabian Beutel, Duesseldorf (DE); Emmanouil Sifalakis, Nijmegen (NL); Zhuangzhuang Yu, Delft (NL)

(73) Assignee: STICHTING IMEC NEDERLAND, Eindhoven (NL)

(*) Notice: Subject to any disclaimer, the term of this patent is extended or adjusted under 35 U.S.C. 154(b) by 82 days.

(21) Appl. No.: 18/908,338

(22) Filed: Oct. 7, 2024

(65) Prior Publication Data

US 2025/0114067 A1 Apr. 10, 2025

(30) Foreign Application Priority Data

Oct. 10, 2023 (EP) .................................... 23202862

(51) Int. Cl.
*A61B 8/08* (2006.01)

(52) U.S. Cl.
CPC .......... *A61B 8/0891* (2013.01); *A61B 8/0858* (2013.01)

(58) Field of Classification Search
CPC ... A61B 8/0891; A61B 8/0858; A61B 8/5207; A61B 8/5223; G16H 50/30
See application file for complete search history.

(56) References Cited

U.S. PATENT DOCUMENTS

| | | | | |
|---|---|---|---|---|
| 2012/0078099 A1* | 3/2012 | Suri | A61B 8/483 600/440 |
| 2019/0076113 A1 | 3/2019 | Palanisamy et al. | |
| 2019/0380677 A1 | 12/2019 | Ono et al. | |

(Continued)

FOREIGN PATENT DOCUMENTS

| | | |
|---|---|---|
| CN | 110136157 A | 8/2019 |
| CN | 111325202 A | 6/2020 |

OTHER PUBLICATIONS

Beutel et al: "P64 Carotid Artery Tracking with Automated Wall Position Resets Yields Robust Distension Waveforms in Long-term Ultrasonic Readings", Artery Research, vol. 25, pp. S106-S107, 2019.

(Continued)

*Primary Examiner* — Bo Joseph Peng
(74) *Attorney, Agent, or Firm* — MOSER TABOADA

(57) ABSTRACT

A method for determining a cross-sectional width of an artery comprises: receiving a time sequence of sets of ultrasound data, each set representing reflection of ultrasound along a line extending through tissue including the artery at a single point in time in the time sequence; and for each set of ultrasound data: determining, using a machine learning model, a region of interest within the ultrasound data, wherein the region of interest is determined using one or more kernels being compared to the ultrasound data, wherein each kernel represents a first wall portion at a first side of a cross-section of the artery, a second wall portion at a second side of the cross-section of the artery, and a lumen in-between; and determining the cross-sectional width of the artery based on analysis of the region of interest of the ultrasound data.

16 Claims, 5 Drawing Sheets

(56) References Cited

U.S. PATENT DOCUMENTS

2021/0045710 A1* 2/2021 Bedi ........................ A61B 8/12
2023/0148992 A1 5/2023 Isla et al.

OTHER PUBLICATIONS

Yousefzadeh et al: Training for Temporal Sparsity in Deep Neural Networks, Application in Video Processing, arXiv:2107.07305v1, pp. 1-18, 2021.
Stuijt et al: "μBrain: An Event-Driven and Fully Synthesizable Architecture for Spiking Neural Networks", Frontiers in Neuroscience, vol. 15, pp. 1-15, 2021.
Wu et al: "Machine learning for diagnostic ultrasound of triple-negative breast cancer", Breast Cancer Research and Treatment, 173, pp. 365-373, 2019.
Xu et al: "Medical breast ultrasound image segmentation by machine learning", Ultrasonics 91, pp. 1-9, 2019.
Delsanto et al: "Characterization of a Completely User-Independent Algorithm for Carotid Artery Segmentation in 2-D Ultrasound Images", IEEE Transactions on Instrumentation and Measurement, vol. 56, No. 4, pp. 1265-1274, 2007.
Übeyli et al: "Wavelet-Based Neural Network Analysis of Internal Carotid Arterial Doppler Signals", Journal of Medical Systems, vol. 30, pp. 221-229, 2006.
Hasegawa et al: "Detection of Lumen-Intima Interface of Posterior Wall for Measurement of Elasticity of the Human Carotid Artery", IEEE Transactions on Ultrasonics, Ferroelectrics, and Frequency Control, vol. 51, pp. 93-108, 2004.
Carvalho et al: "Lumen Segmentation and Motion Estimation in B-mode and Contrast-Enhanced Ultrasound Images of the Carotid Artery in Patients with Atherosclerotic Plaque", IEEE Transactions on Medical Imaging, pp. 1-12, 2014.
Sifakis et al: "Robust Carotid Artery Recognition in Longitudinal B-Mode Ultrasound Images", IEEE Transactions on Image Processing, vol. 23, No. 9, pp. 3762-3772, 2014.
Lekadir et al: "A Convolutional Neural Network for Automatic Characterization of Plaque Composition in Carotid Ultrasound", IEEE Journal of Biomedical and Health Informatics, vol. 21, pp. 1-25, 2017.
Yu: "Machine Learning of Ultrasound Data: Cardiovascular Parameters Detection Using Carotid Artery Measurement", Thesis presentation; https://link.edgepilot.com/s/17402818/P-q2SSBC5UqSXreSwCEJAw?u=https://repository.tudelft.nl/record/auid:593afe25-c76d-4dc7-b1b8-81a9b4ec617e; retrieved on Aug. 31, 2023, 2 pages.
Venugopal: "Automatic Arterial Wall Detection and Diameter Tracking using M-mode Ultrasound", Master Thesis, Carleton University, Ottawa, Ontario, Canada, 2019, 219 pages.
Nabeel et al: "Deep Learning for Blood Pressure Estimation: an Approach using Local Measure of Aterial Dual Diameter Waveforms", 2019 IEEE International Symposium on Medical Measurements and Applications, Istanbul, Turkey, pp. 1-6, 2019.
Sahani et al: "A Machine Learning Pipeline for Measurement of Arterial Stiffness in A-mode Ultrasound", IEEE Transactions on Ultrasonics, Ferroelectronics, and Frequency Control, vol. 69, No. 1, pp. 106-113, 2022.
Singh et al: "A Machine Learning Approach to Carotid Wall Localization in A-mode Ultrasound", 2020 IEEE International Symposium on Medical Measurements and Applications, pp. 1-5, 2020.
Extended European Search Report for Application No. EP23202862.1 dated Feb. 16, 2024, 8 pages.

* cited by examiner

METHOD, A COMPUTER PROGRAM PRODUCT, AND A DEVICE FOR DETERMINING A CROSS-SECTIONAL WIDTH OF AN ARTERY

CROSS-REFERENCE TO RELATED APPLICATIONS

The present application claims the benefit of and priority to EP Patent Application Serial No. 23202862.1, filed Oct. 10, 2023, the entire contents of which is incorporated herein by reference.

TECHNICAL FIELD

The present description relates to determining a cross-sectional width of an artery. The cross-sectional width may further be used for determining a biomarker.

BACKGROUND

Cardiovascular diseases are the leading cause of mortality globally. Thus, there is a large need for efficient detection of cardiovascular diseases.

Ultrasound measurements are frequently used for identifying cardiovascular diseases. For instance, ultrasound measurements may be used for examining arteries, such as the carotid artery, for monitoring changes to the diameter during a cardiac cycle. This may be useful, for example, as an indication of abnormal arterial stiffness, which may be related to various cardiovascular diseases.

However, the determining of the diameter of an artery from ultrasound measurements is typically performed by a professional operator. Thus, analysis of the ultrasound measurements may be time consuming and require manual labor.

It would be desirable to provide an automated determination of the diameter of the artery, so that manual analysis may be avoided. It would further be desirable to provide automated determination with a low requirement on processing resources. In particular, this may imply that the automated determination of the diameter of the artery is possible to perform in a wearable device.

SUMMARY

An objective of the present description is to enable automated determination of a diameter of an artery. A further objective is to enable automated determination with low requirements on processing resources.

These and other objectives of the present description are at least partly achieved by the invention as defined in the independent claims. Preferred embodiments are set out in the dependent claims.

According to a first aspect, there is provided a method for determining a cross-sectional width of an artery, said method comprising: receiving a time sequence of sets of ultrasound data, each set representing reflection of ultrasound along a line extending through tissue including the artery at a single point in time in the time sequence; and for each set of ultrasound data: determining, using a machine learning model, a region of interest within the ultrasound data, wherein the region of interest is determined using one or more kernels being compared to the ultrasound data, wherein each kernel represents a first wall portion at a first side of a cross-section of the artery, a second wall portion at a second side of the cross-section of the artery, and a lumen between the first and the second wall portions; and determining the cross-sectional width of the artery based on analysis of the region of interest of the ultrasound data.

It is an insight of the present description that the ultrasound data has a very distinct pattern corresponding to the artery, being defined by two wall portions surrounding the lumen in-between the wall portions. Thus, the method utilizes one or more kernels that represent the pattern in ultrasound data corresponding to the artery. Thanks to the method using such kernel(s), a robust determination of the region of interest in the ultrasound data is enabled. Thus, the method is very accurate in determining the region of interest and is able to correctly identify the region of interest in the ultrasound data corresponding to the artery. For instance, the method is able to correctly determine the region of interest even if signal levels of the region of interest are lower than noise from other structures in tissue than the artery.

Since the method utilizes the very distinct pattern of the artery in ultrasound data, the method may use very few kernels, or even just one kernel, for comparison to the ultrasound data. This implies that the processing needed is computationally efficient and requires a low amount of processing resources, since a small amount of data needs to be processed for finding the region of interest.

In addition, thanks to the region of interest being determined, relevant data is extracted from the ultrasound data. This implies that the entire set of ultrasound data need not be further processed. Rather, the determining of the cross-sectional width of the artery may be performed merely on the region of interest, such that the determining of the cross-sectional width may also be computationally efficient.

Thanks to the method requiring low amount of processing resources, it is feasible to implement the method in a processing unit that may be arranged in a wearable device. Thus, the method may be implemented in a device which may be worn by a subject, which may facilitate real-time monitoring of the cross-sectional width of the artery. However, it should be realized that the method need not necessarily be performed in a wearable device. Rather, the method could be performed in a device separate from an ultrasound sensor that acquires the ultrasound data.

The cross-sectional width of the artery may be a useful biomarker for monitoring health of a subject. In particular, a change of the cross-sectional width over time, such as the changes of the cross-sectional width during a time period corresponding to a heartbeat, may provide insight to the health of a subject.

It should be realized that the cross-sectional width may correspond to the diameter of the artery. However, the line extending through the artery may not be exactly aligned with the diameter of the artery. The cross-sectional width may still provide useful information even if the cross-sectional width does not exactly correspond to the diameter. Since the time sequence represent the same line extending through tissue during different points in time, the changes of the cross-sectional width over time may still provide useful information even if the cross-sectional width does not correspond to the diameter.

Each set of ultrasound data may be acquired based on a pulse of ultrasound being reflected by the tissue including the artery. The reflected ultrasound pulse may carry information of structure of the tissue. Time of arrival of reflected ultrasound corresponds to a distance traveled by the ultrasound along the line. The reflected ultrasound pulse may be detected so as to form ultrasound data, wherein ultrasound signals at different times of arrival represent different depths in tissue along the line.

Each set of ultrasound data may correspond to a single pulse of ultrasound and may hence represent ultrasound reflection of the single pulse of ultrasound. Thus, each set of ultrasound data may form a representation at a time instance corresponding to the single pulse of ultrasound. The time sequence of sets of ultrasound data may be formed based on sequential ultrasound pulses. Hence, even though each set of ultrasound data may be detected by detecting reflected ultrasound during a range of times of arrival of the reflected ultrasound, the set of ultrasound data still represents the tissue and artery at a single point in time. The points in time of different sets of ultrasound data are distinct and correspond to respective pulses of ultrasound being reflected by the tissue including the artery. The time sequence of sets of ultrasound data may thus represent a plurality of sets of ultrasound data, wherein the sets of ultrasound data are sequential in time.

In embodiments, each set of ultrasound data may be referred to as A-mode ultrasound. In embodiments, the time sequence of sets of ultrasound data may be referred to as M-mode ultrasound.

The machine learning model may be based on supervised training. The machine learning model may be an artificial neural network. The use of kernel(s) representing the distinct pattern of ultrasound data corresponding to the artery allows use of a simple artificial neural network. Thus, the machine learning model may be an artificial neural network with few layers, such as only three layers.

The machine learning model may be based on training for a population or for a specific individual. The machine learning model may alternatively be based on training for a population, wherein the model is further updated by additional training on the specific individual so as to personalize the model.

It should be realized that the artery may be formed by a wall surrounding a lumen. In a cross-section of the artery, the wall has different wall portions on opposite sides of the lumen. Thus, the first wall portion and the second wall portion may be arranged on opposite sides of the lumen in the cross-section of the artery.

The ultrasound data may correspond to a cross-section of the artery, wherein the cross-section may be perpendicular to a longitudinal direction of the artery extending along a center of the lumen. However, it should be realized that the cross-section may not be exactly perpendicular to the longitudinal direction of the artery. This would imply that the cross-sectional width would be slightly larger than a diameter of the artery. It should further be realized that the line extending through the artery may not go exactly through a center of the lumen, such that the line may correspond to a chord through the artery. This would imply that the cross-sectional width would be slightly smaller than a diameter of the artery.

The method may be used for determining the cross-sectional width of an artery of a human being. For instance, the method may be used for determining the cross-sectional width of a carotid artery. However, it should be realized that the method may alternatively be used for determining the cross-sectional width of an artery of an animal being.

According to an embodiment, the method further comprises pre-processing each set of ultrasound data to form a univariate representation of an ultrasound response from the tissue including the artery.

Thus, the ultrasound data may comprise a single variable representing tissue and artery along the line in which ultrasound response is acquired. This implies that a small amount of data needs to be processed for determining the region of interest.

According to an embodiment, the pre-processing comprises extracting an envelope of the ultrasound response using a Hilbert transform and computing a magnitude of the envelope.

This is a suitable manner for forming the univariate representation of the ultrasound response.

The magnitude of the envelope provides a distinct pattern corresponding to the artery. The magnitude of the envelope has a small value within the lumen of the artery, whereas the magnitude of the envelope has a high value at the wall portions. Thus, the kernel(s) may be represented as two peaks having high values with a region having a small value between the peaks.

According to an embodiment, the determining of the cross-sectional width is based on the univariate representation of the ultrasound response in the region of interest.

Thus, the same representation of the ultrasound response may be used both for determining the region of interest and, thereafter, for determining the cross-sectional width of the artery.

It has been found that the determining of the cross-sectional width is more robust when using the univariate representation, such as a magnitude of the envelope acquired by the Hilbert transform, compared to using raw ultrasound data.

According to an embodiment, determining the cross-sectional width of the artery is performed using a machine learning model which is configured to receive the region of interest of the ultrasound data.

This may allow the cross-sectional width to be accurately determined. Further, the determining of the cross-sectional width of the artery may be provided with low requirement on processing resources, since only the region of interest of the ultrasound data need to be used as input to the machine learning model.

The machine learning model for determining the cross-sectional width of the artery is different from the machine learning model for determining the region of interest.

The machine learning model for determining the region of interest (ROI) may be referred to herein as ROI machine learning model, whereas the machine learning model for determining the cross-sectional width (CSW) may be referred to herein as CSW machine learning model.

The CSW machine learning model may be based on training for a population or for a specific individual. The CSW machine learning model may alternatively be based on training for a population, wherein the model is further updated by additional training on the specific individual so as to personalize the model.

The CSW machine learning model may be based on supervised training. The CSW machine learning model may be an artificial neural network.

However, it should be realized that the cross-sectional width need not necessarily be determined using a machine learning model. Rather, according to an alternative, the cross-sectional width may be determined by analytically processing the ultrasound data of the region of interest. For instance, the cross-sectional width may be determined using digital signal processing.

According to an embodiment, determining the cross-sectional width of the artery is performed individually for each set of ultrasound data by the machine learning model.

Thus, the determining of the cross-sectional width at a single point in time in the time sequence does not take into account cross-sectional widths determined at other points in time in the time sequence. The CSW machine learning model may alternatively use the determined cross-sectional widths in other points in time, such as using a recurrent neural network. However, it has been found that an artificial neural network that only considers ultrasound data of a single point in time provides a better performance for accurately determining the cross-sectional width.

According to an embodiment, the method further comprises applying a smoothing process to a time sequence of determined cross-sectional widths based on the sets of ultrasound data.

This may ensure that a smoothness of the time sequence of determined cross-sectional widths is provided even though the cross-sectional widths are individually determined.

Further analysis of the time sequence of cross-sectional widths for determining indication(s) of a health condition of the subject may involve determining a derivative of the time sequence of cross-sectional widths. Use of the smoothing process may enable the derivative to be correctly determined.

According to an embodiment, the one or more kernels comprise a plurality of convolution kernels, wherein each convolution kernel corresponds to a respective size of the artery and represent values in the ultrasound data forming two peaks of high values separated by low values in between the peaks.

The convolution kernels may include a kernel corresponding to a maximum anticipated size of the artery. Such kernel may correspond to the maximum anticipated size of the artery in a population excluding outliers.

The plurality of kernels may be used for reinforcing a depth of the lumen center within the tissue so as to reinforce the accurate detection of the region of interest. Thus, the kernels may be used in combination for determining the region of interest.

The plurality of kernels may comprise kernels for taking into account a variation or range of the maximum size of the artery across a population. The number of kernels may depend on how much the size of the artery varies.

According to an embodiment, the plurality of kernels comprises two to five kernels, such as three kernels.

According to an embodiment, the machine learning model for determining the region of interest comprises at least two convolution layers, wherein a first layer uses the plurality of convolution kernels, and a second layer forms an average of output from each of the plurality of convolution kernels in the first layer.

This may be a suitable manner for efficiently determining the region of interest taking the plurality of convolution kernels into account.

According to an embodiment, further comprising processing the time sequence of sets of ultrasound data using a machine learning model, for identifying a segment in the time sequence corresponding to a cardiac cycle.

Changes of the cross-sectional width of the artery during a cardiac cycle may be of particular interest for determining a health condition of the subject. Thus, identifying of a segment in received data corresponding to the cardiac cycle may be useful in analyzing health of the subject.

The method may advantageously use a machine learning model for identifying the segment corresponding to the cardiac cycle. This is a robust manner of determining the segment.

The machine learning model for identifying the segment corresponding to the cardiac cycle is different from the ROI machine learning model and the CSW machine learning model. The machine learning model for identifying the segment corresponding to the cardiac cycle (CC) may be referred to herein as CC machine learning model.

According to an embodiment, the method comprises receiving a plurality of parallel time sequences of sets of ultrasound data representing reflection of ultrasound along parallel lines in different cross sections of the artery along a longitudinal direction of the artery, wherein each of the parallel time sequences is processed to determine the cross-sectional width of the artery in respective cross-sections.

This may allow the cross-sectional width of the artery to be monitored in several locations along extension of the artery.

The results of the cross-sectional widths from the parallel lines may be combined, which may allow uncertainty to be reduced in monitoring of changes of the cross-sectional width during the time sequence.

According to a second aspect, there is provided a method for determining a biomedical marker, said method comprising the method for determining the cross-sectional width of the artery according to the first aspect and computing a value representing the biomedical marker based on the determined cross-sectional width of the artery in the time sequence.

Effects and features of this second aspect are largely analogous to those described above in connection with the first aspect. Embodiments mentioned in relation to the second aspect are largely compatible with the first aspect.

The biomedical marker may be determined based on the determined cross-sectional width of the artery only. Alternatively, the biomedical marker may be determined based on additional information.

For instance, the biomedical marker may be representative of arterial stiffness. The determined cross-sectional width of the artery in the time sequence for instance be used for computing a pulse arrival time or a pulse wave velocity.

According to a third aspect, there is provided a computer program product comprising computer-readable instructions such that when executed on a processing unit, the computer program product will cause the processing unit to perform the method according to the first or the second aspect.

Effects and features of this third aspect are largely analogous to those described above in connection with the first and second aspects. Embodiments mentioned in relation to the third aspect are largely compatible with the first and second aspects.

The computer program product may implement the method in a processing unit, which may be a dedicated processing unit for performing the method or may be a general-purpose processing unit which may be able to perform the method based on the computer program product. For instance, the processing unit may be embedded in a small apparatus that may be worn by the subject.

The computer program product may comprise a computer-readable medium on which the computer-readable instructions are stored. The computer program product may thus be provided as a non-transient computer program product stored on any tangible medium. Alternatively, the computer program product may be provided as a signal carrying the computer-readable instructions for allowing the computer program product to be loaded into a memory accessible to the processing unit.

The computer program product may have access to a memory storing the machine learning model for determining the region of interest of ultrasound data.

According to a fourth aspect, there is provided a device for determining a cross-sectional width of an artery, said device comprising a processing unit configured to: receive a time sequence of sets of ultrasound data, each set representing reflection of ultrasound along a line extending through tissue including the artery at a single point in time in the time sequence; and for each set of ultrasound data: determine, using a machine learning model, a region of interest within the ultrasound data, wherein the region of interest is determined using one or more kernels being compared to the ultrasound data, wherein each kernel represents a first wall portion at a first side of a cross-section of the artery, a second wall portion at a second side of the cross-section of the artery, and a lumen between the first and the second wall portions; and determine the cross-sectional width of the artery based on analysis of the region of interest of the ultrasound data.

Effects and features of this fourth aspect are largely analogous to those described above in connection with the first, second, and third aspects. Embodiments mentioned in relation to the fourth aspect are largely compatible with the first, second, and third aspects.

The device is configured to process the ultrasound data in a computationally efficient manner such that a low amount of processing resources is required. Thus, the device may be provided as a wearable device with the processing unit arranged in the wearable device.

According to an embodiment, the device further comprises an ultrasound sensor configured to be arranged in relation to the tissue including the artery, to emit ultrasound into the tissue, to detect the time sequence of sets of ultrasound data, and to transfer the time sequence of sets of ultrasound data to the processing unit.

Thus, the device may further comprise the ultrasound sensor for acquiring the ultrasound data. The ultrasound sensor and the processing unit may be arranged in a common physical housing.

However, it should be realized that the processing unit need not necessarily be arranged together with the ultrasound sensor. Rather, the device may comprise a communication unit, which is configured to receive the ultrasound data through wired or wireless communication with a communication unit associated with the ultrasound sensor.

The processing unit may be provided in a wearable device that may facilitate that a subject wearing the device may be presented with a measure of cardiovascular health in the wearable device in real time. Thus, the subject may continuously check information of a health condition. The processing unit may be arranged in a device that the subject may anyway wear, such as in a smartwatch.

Alternatively, the processing unit may be provided in a unit that may not necessarily be worn by the subject, but which may be available for short-range communication with the ultrasound sensor, such as the processing unit being arranged in a smartphone.

As a further alternative, the processing unit may be provided anywhere, such as "in the cloud". The processing unit may communicate with the ultrasound sensor through a computer network, such as the Internet, enabling the processing unit to be arranged anywhere in relation to the ultrasound sensor. The processing unit may communicate results of the determination of the cross-sectional width of the artery back to the subject to enable presentation to the subject, e.g., communicating to a smartphone or to a wearable device.

BRIEF DESCRIPTION OF THE DRAWINGS

The above, as well as additional objects, features, and advantages of the present description, will be better understood through the following illustrative and non-limiting detailed description, with reference to the appended drawings. In the drawings like reference numerals will be used for like elements unless stated otherwise.

DETAILED DESCRIPTION

Figure 1:
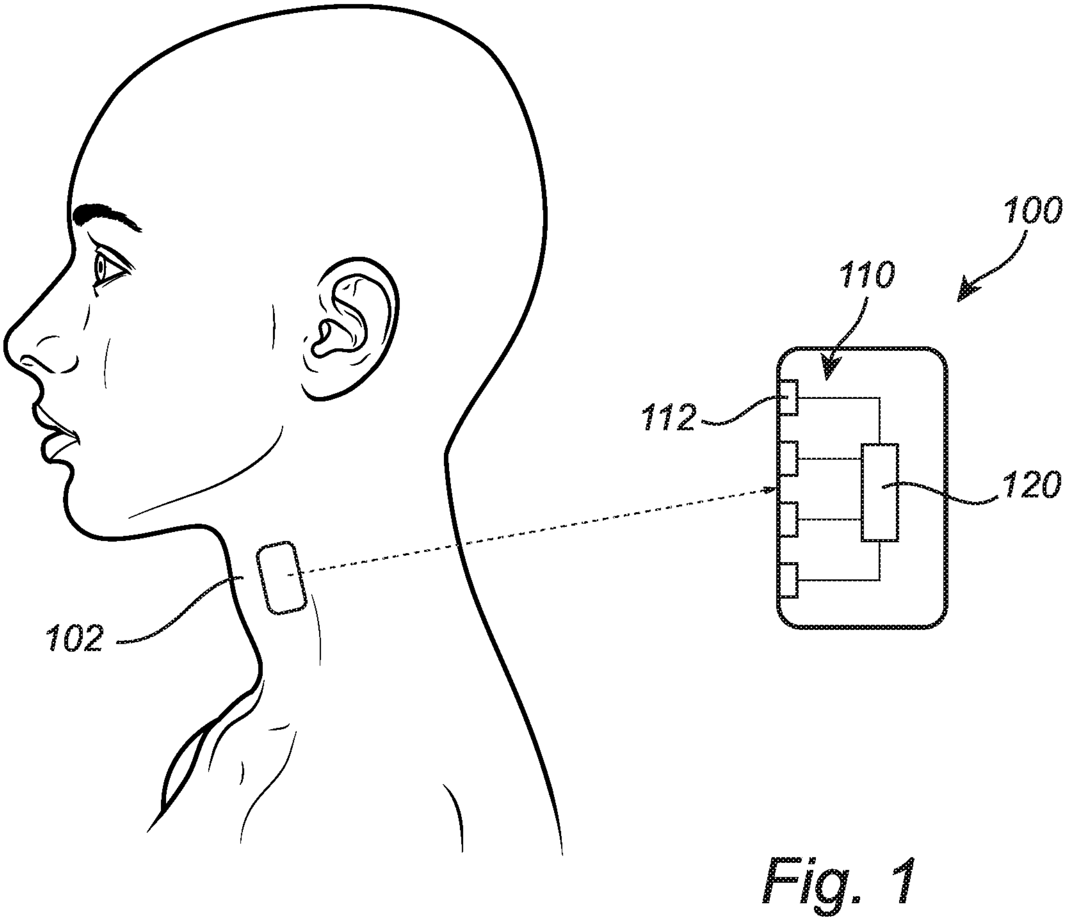
FIG. 1 is a schematic view of a device for determining a cross-sectional width of an artery according to an embodiment.

Referring now to FIG. 1, a device 100 which may be used for estimating a measure of cardiovascular health of a subject 102 is described. The device 100 is configured to determine a cross-sectional width of an artery, which may further be used for estimating the measure of cardiovascular health.

The device 100 may comprise an ultrasound sensor 110. The ultrasound sensor 110 may be configured to acquire an ultrasound signal representing reflection of ultrasound along a line extending through tissue including the artery.

The ultrasound sensor 110 may be configured to be arranged in relation to a location in the artery of the subject 102 for acquiring the ultrasound signal. For instance, the ultrasound sensor 110 may be configured to be arranged in contact with the skin of the subject 102 at the location of the artery, such as being arranged at a neck of the subject 102 for acquiring the ultrasound signal from the carotid artery.

According to an embodiment, the ultrasound sensor 110 may be arranged in or on a carrier, which may be configured to adhere to the skin of the subject 102, such as in the form of a patch, or which may be configured to be arranged in relation to a body part, such as around the neck, the torso, or a wrist.

The ultrasound sensor 110 may be configured to emit ultrasound into tissue including the artery and to detect an ultrasound response. According to an embodiment, the ultrasound sensor 110 may comprise at least one, such as a plurality of micromachined ultrasonic transducers (MUT), such as capacitive cMUTs or piezoelectric pMUTs. Each MUT may be used for generating an electric signal based on receiving the ultrasound signal from a line extending through tissue including the artery. Using MUTs may facilitate the ultrasound sensor 110 being compact and possible to be arranged on a small carrier.

The ultrasound sensor 110 may use ultrasound transducer (s) for both emitting ultrasound into tissue and for detecting the ultrasound response. A plurality of ultrasound transducers may be arranged in a linear array allowing ultrasound response to be detected in a plurality of parallel lines. However, it should be realized that the ultrasound sensor 110 may be configured to detect ultrasound from a single line. For brevity, only a single ultrasound transducer 112 will now be discussed.

The ultrasound transducer 112 may be configured to emit pulses of ultrasound. Each pulse may travel into tissue and cause a reflection of the emitted ultrasound. The reflected ultrasound may then be detected by the ultrasound transducer. Time of arrival of the reflected ultrasound corresponds to a reflection at a particular depth into the tissue.

Each ultrasound pulse may thus cause reflection of ultrasound which may be detected by the ultrasound transducer 112. The ultrasound transducer 112 may thus detect a signal which may be used for identifying the artery in tissue and which may further be used for determining the cross-sectional width of the artery.

The ultrasound transducer 112 may be configured to emit ultrasound having a frequency in a range of 1-20 MHz, such as 2-10 MHz. This implies that a spatial resolution of detecting features within tissue is in a range of fraction of millimeters, such as 0.1 mm. Hence, acquired ultrasound data may be used for accurately determining the cross-sectional width of the artery.

The ultrasound transducer 112 may have a sampling frequency at which pulses are output from the ultrasound transducer 112. Thus, for each pulse a separate measurement may be performed allowing the cross-sectional width of the artery to be determined at a point in time associated with the pulse.

The sampling frequency may for instance be in a range of 100-1000 Hz, such as 400-600 Hz, allowing the cross-sectional width of the artery to be accurately tracked.

Figure 2:
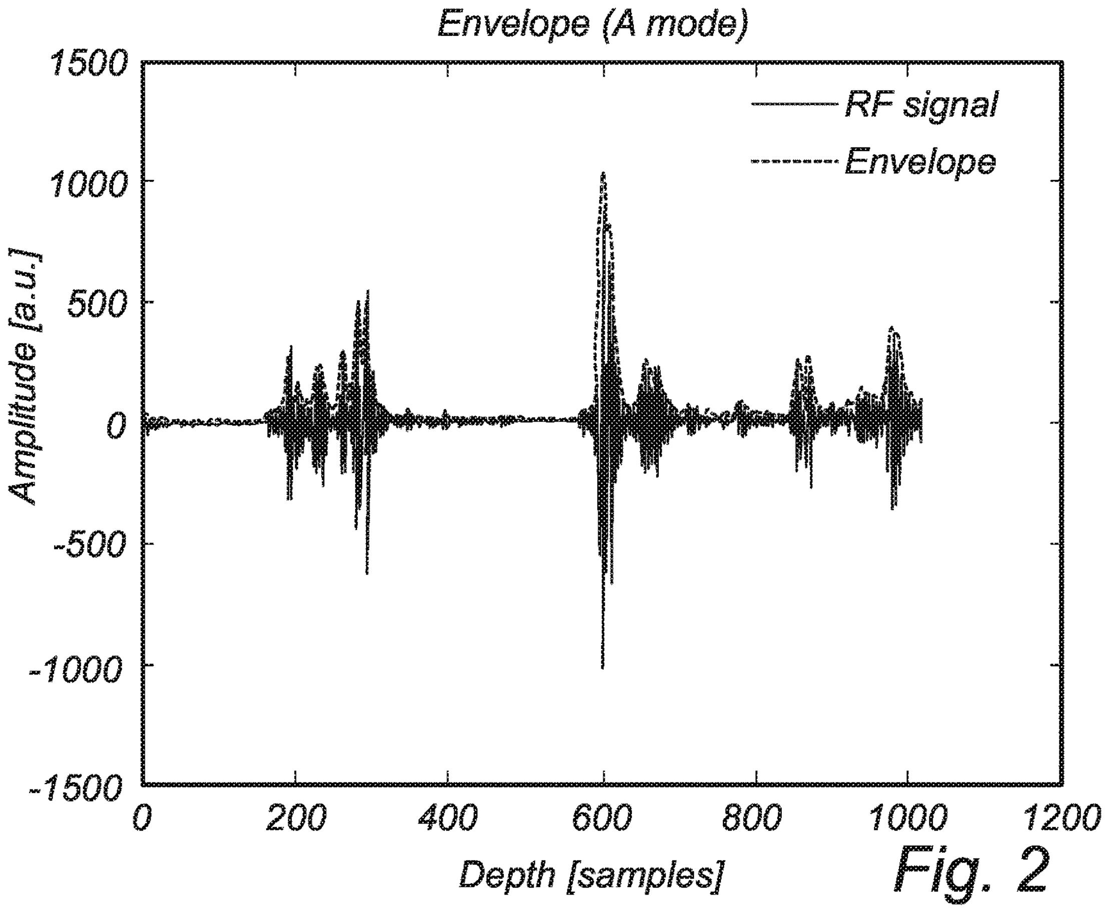
FIG. 2 is an example of a set of ultrasound data.

Referring now to FIG. 2, the ultrasound signal detected for a single pulse is illustrated. The ultrasound transducer 112 may generate a radio frequency electric signal in response to receiving ultrasound, as illustrated in FIG. 2.

The ultrasound transducer 112 may thus detect a set of ultrasound data for each single pulse. The set of ultrasound data may be associated with a time point at which the pulse is emitted, such that the set of ultrasound data corresponds to a single point in time. The set of ultrasound data may be an A-mode frame of ultrasound data.

Figure 3:
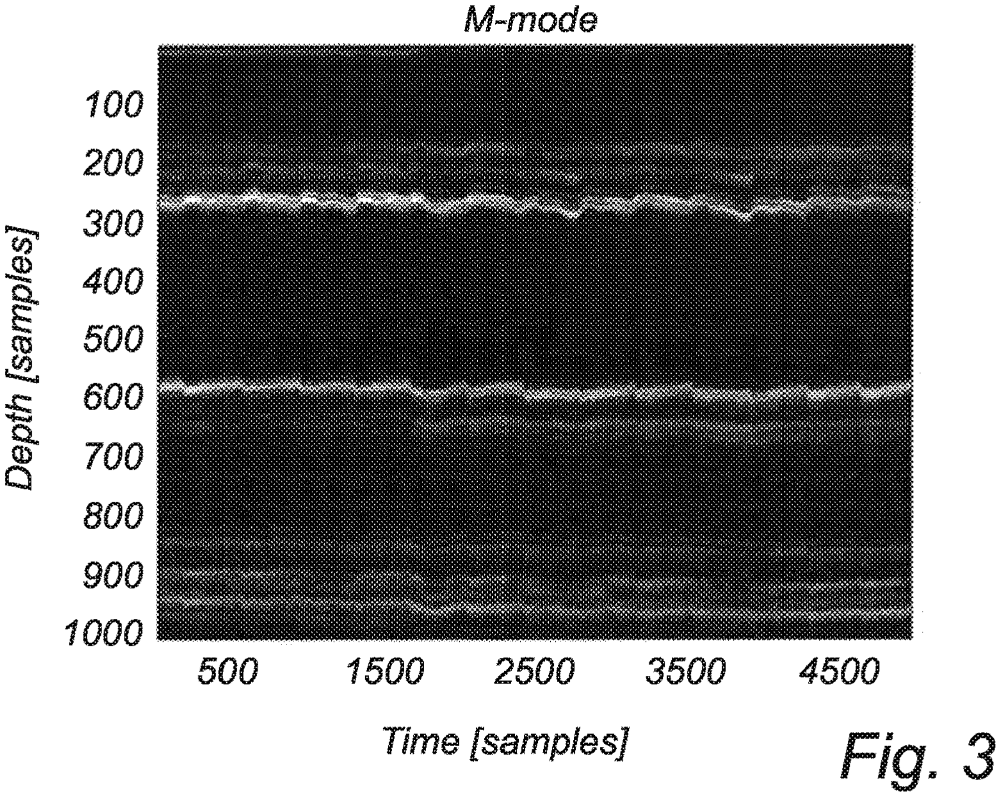
FIG. 3 is an example of a time sequence of sets of ultrasound data.

In addition, the ultrasound signal may be detected for each pulse. Thus, a time sequence of sets of ultrasound data may be detected. Referring now to FIG. 3, the sets of ultrasound data may be presented as a chart, wherein a single point in time corresponds to a point on the x-axis of the chart. The y-axis represents depth into tissue and a brightness of a point in the chart represents amplitude of the ultrasound signal.

The ultrasound transducer 112 may thus be configured to detect the time sequence of sets of ultrasound data. This time sequence may be M-mode data of ultrasound detection.

As illustrated in FIGS. 2 and 3, the depth in tissue is represented as samples. This relates to a sampling rate of the ultrasound transducer 112. Sample values may be converted to a distance based on sampling rate and speed of ultrasound in tissue. In the case illustrated in FIGS. 2 and 3, a sampling rate of 31.25 MHz was used. In combination with a propagation speed of ultrasound in tissue corresponding to 1540 m/s and taking into account that ultrasound has traveled from the ultrasound transducer 112 into tissue and back again to the ultrasound transducer 112, a depth presented in samples should be multiplied by 24.65 μm to obtain the corresponding distance. In addition, the time sequence of sets of ultrasound data is acquired with a sampling frequency of 500 Hz, such that the time presented in samples in FIG. 3 should be multiplied by 0.002 s to obtain a corresponding point in time.

The device 100 further comprises a processing unit 120. The processing unit 120 is configured to receive the time sequence of sets of ultrasound data. The processing unit 120 may communicate with the ultrasound sensor 110, such that the ultrasound sensor is configured to transfer the time sequence of sets of ultrasound data to the processing unit 120.

The processing unit 120 is further configured to process the time sequence of sets of ultrasound data in order to determine a cross-sectional width of the artery, as will be further described below.

The processing unit 120 may be arranged in a common housing with the ultrasound sensor 110. However, according to an alternative, the processing unit 120 may be arranged separately from the ultrasound sensor 110 and may be arranged to communicate with the ultrasound sensor 110 through wired or wireless communication for receiving the time sequence of sets of ultrasound data.

The processing unit 120 may for instance be arranged in a wearable device enabling the processing unit 120 to be worn by the subject 102. The device 100 may be formed in its entirety as a wearable device such that the subject 102 may freely move while measurements are performed, and the cross-sectional width of the artery is determined.

According to an alternative, the processing unit 120 may be arranged in a server "in the cloud" and the ultrasound sensor 110 may be configured to communicate with the processing unit 120 through the Internet.

The processing unit 120 may be a central processing unit (CPU), which may execute the instructions of one or more computer programs in order to process the time sequence of sets of ultrasound data. The processing unit 120 may also control functionality of the ultrasound sensor 110 such as for triggering start of acquisition of ultrasound data.

The processing unit 120 may alternatively be implemented as firmware arranged e.g. in an embedded system, or as a specifically designed process-ing unit, such as an Application-Specific Integrated Circuit (ASIC) or a Field-Programmable Gate Array (FPGA), which may be configured to implement functionality for processing the time sequence of sets of ultrasound data.

Figure 4:
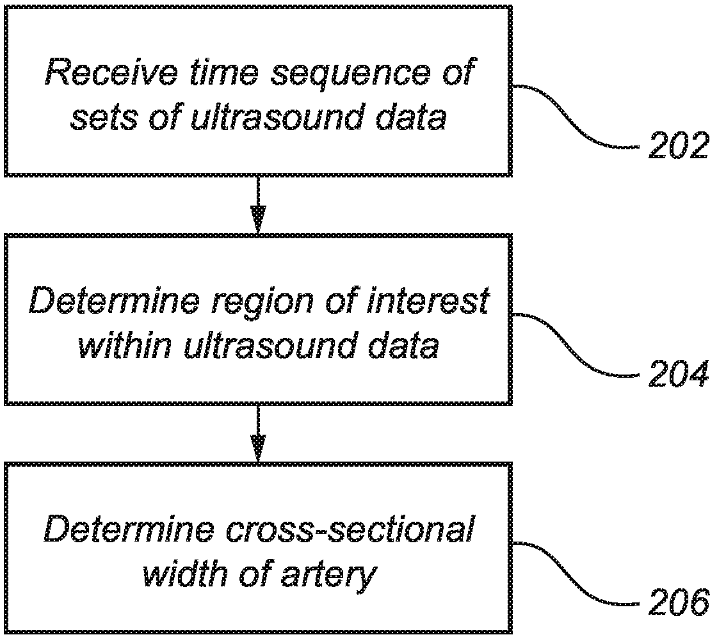
FIG. 4 is a flow chart of a method according to an embodiment.

Referring now to FIG. 4, a method for determining the cross-sectional width of an artery will be discussed in more detail. As mentioned above, the method may be implemented by a computer program product comprising computer-readable instructions being executed on a processing unit, or by processing performed by a specifically designed processing unit.

The method comprises receiving 202 a time sequence of sets of ultrasound data.

The method comprises, for each set of ultrasound data, determining 204 a region of interest within the ultrasound data, and determining 206 the cross-sectional width of the artery based on analysis of the region of interest. Thus, the method allows tracking of the cross-sectional width of the artery by the cross-sectional width being determined for the points in time within the time sequence.

Thanks to determining a region of interest, the cross-sectional width of the artery may be determined only on part of the ultrasound data, allowing the determining of the cross-sectional width to be computationally efficient since only relevant data needs to be processed.

It should be realized that the cross-sectional width of the artery may be a diameter of the artery. However, if the line along which ultrasound information is detected is not aligned with a center of the artery in a cross-section of the artery perpendicular to a longitudinal extension of the artery, the cross-sectional width may not correspond exactly to the diameter. For instance, a chord through the artery may be acquired or a line extending through an oblique cross-section of the artery may be acquired. Tracking of the cross-sectional width in the time sequence may still give important information of cardiovascular health of the subject 102. For simplicity and brevity, reference is made below to a diameter of the artery, but it should be realized that another cross-sectional width of the artery may be analyzed.

Each set of ultrasound data may initially be pre-processed. The raw ultrasound data may be pre-processed to form a univariate representation of ultrasound response from the tissue. This implies that raw ultrasound data may be smoothed, which may facilitate further processing of the ultrasound data.

The pre-processing may comprise extracting an envelope of the ultrasound response. This may be performed by using a Hilbert transform on the raw ultrasound data. The envelope may alternatively be determined using a fast Fourier transform on the raw ultrasound data. Then, a magnitude of the envelope may be computed to form the univariate representation.

The envelope forms a smoothed interpolation of the raw ultrasound data. This may further allow subsampling of the envelope, such that an amount of data may be reduced. Such subsampling may thus reduce complexity of further processing which is beneficial for computational economy.

The determining 204 of a region of interest within the ultrasound data may be performed using a machine learning model, hereinafter referred to as a ROI machine learning model.

The region of interest is determined using one or more kernels being compared to the ultrasound data. Each kernel represents a first wall portion at a first side of a cross-section of the artery, a second wall portion at a second side of the cross-section of the artery, and a lumen between the first and the second wall portions.

Thus, the ROI machine learning model exploits a heuristic that the lumen of the artery is a hypoechogenic area whose center is most quiescent part of reflection of ultrasound signals. Thus, one or more kernels representing the specific pattern of the ultrasound response from the wall portions of the artery and the lumen in-between are used in the ROI machine learning model.

The ROI machine learning model may be configured to identify a center of the lumen within the ultrasound data and may further be configured to determine the region of interest as a window that is centered around the lumen center. The lumen center may be identified as a distance to the ultrasound transducer 112.

The kernels may be one-dimensional arrays of values representing two peaks of high values separated by low values (such as 0 or slightly above 0, e.g., 0.001) between the peaks. The sizes of the kernels relate to a maximum possible anticipated diameter of the artery and the kernels should therefore be "wide" enough to account for demographic physiological variability across different subjects. The number of kernels can be used to account for spatial variability between the maximum and minimum diameter of the lumen as the artery expands. However, since the number of kernels is then merely used to reinforce the depth of the lumen center, only a small number of kernels suffices. For instance, 3 kernels may be used, thereby significantly confining the number of required parameters to be trained in the ROI machine learning model as well as the number of computations when the ROI machine learning model is deployed.

The kernels may be convolution kernels to be used in a convolution layer of an artificial neural network.

Figure 5:
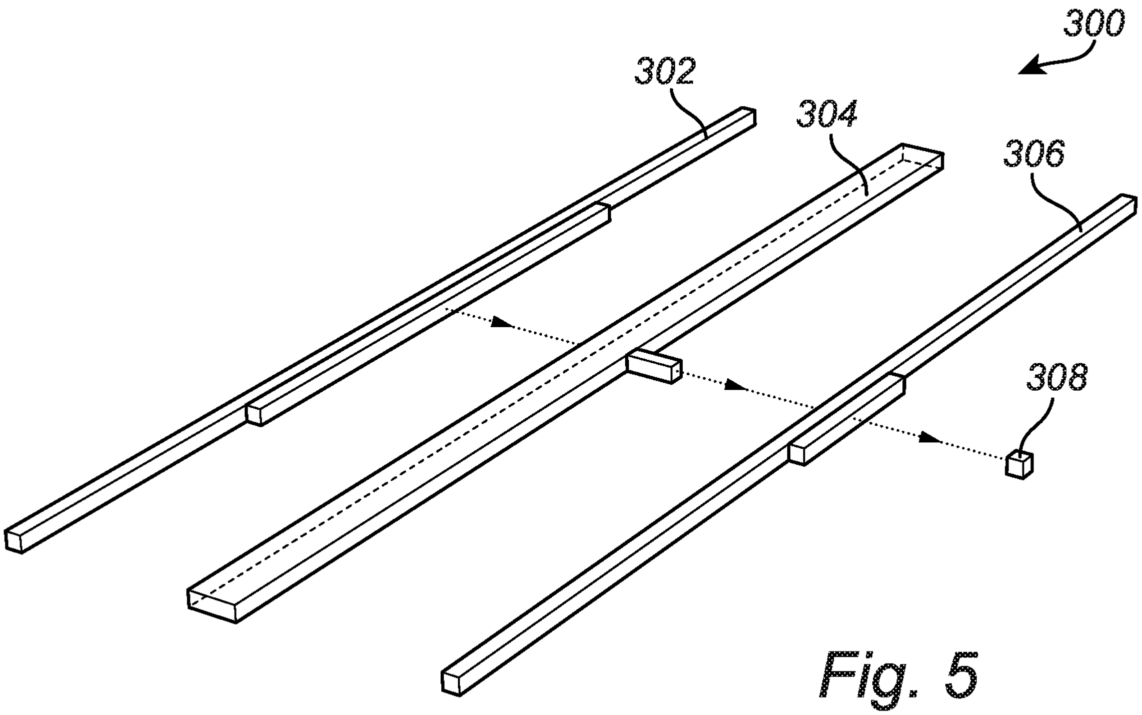
FIG. 5 is a schematic view of machine learning model for determining a region of interest within ultrasound data.

The ROI machine learning model may be formed as a small neural network architecture that can be trained using a small amount of training data. Referring now to FIG. 5, an embodiment of the ROI machine learning model is shown. As shown in FIG. 5, a neural network architecture 300 may comprise two convolution layers 302, 304.

The neural network 300 may thus have a first convolution layer 302 which uses the kernels described above. Each node in the convolution layer 302 may thus compute a convolution of input ultrasound data and the kernel.

The neural network 300 may further have a second convolution layer 304 which receives output from the first convolution layer 302 as input to the second convolution layer 304. The second convolution layer 304 may use a small 1×1 kernel that summarizes the inputs from the first convolution layer 302 providing information at each depth position for each kernel in the first convolution layer 302, with depth-wise convolution.

The two convolutional layers 302, 304 may be followed by a parameterless average pooling filter layer 306 that smoothens distance estimates to the lumen center by using information across a small neighborhood of depths.

Finally, the neural network 300 may be configured to find a best estimate of the distance to the lumen center based on the distance estimates. This may be performed by a simple operation 308 to find a maximum argument (argmax) of the distance estimates form the pooling filter layer. The operation 308 produces the estimated position of the lumen center.

Once the position of the lumen center has been found, a clipping window may be applied centered around the position of the lumen center. The clipping window may thus define the region of interest by centering around the position of the lumen center. The size of the clipping window may match the sizes of the kernels of the first convolutional layer.

This machine learning model provides a very simple manner of finding the region of interest by centering the region of interest around the lumen center. It should be realized that the machine learning model may alternatively be configured to also identify a size of the region of interest to be used such that different sizes of the region of interest may be provided in dependence of a size of the artery. However, this may need further layers in the artificial neural network.

In training of the ROI machine learning model, a dataset was built based on data acquired from 6 human subjects (4 male, 2 female, 38±10 years of age; mean arterial pressure 86.3±7.6 mmHg). Data was collected in three repeated measurement sessions, spread over three weeks, to account for physiological intra-subject variability as well as technical measurement bias, e.g., due to sensor reattachment and probe repositioning. Each session comprised three interventions. First, 2 minutes in resting condition were recorded for best inter-subject comparability. Second, the subject was asked to perform 2 minutes of paced breathing to induce cyclic blood pressure variation at 7.5 cycles per minute, guided by an acoustic reference signal. Third, to induce a short-term gradual blood pressure increase and hence artery diameter increase, the subject was asked to perform a hand grip dynamometer exercise with the sensor free hand for 1 minute at maximal voluntary contraction, followed by 1 minute of recovery. Overall, this setup provides sufficient variability in terms of number of subjects and physiological conditions as well as length of recordings to produce a reasonably large training data set for general-purpose training, but which also allows exploration of personalization aspects.

For the training of the ROI machine learning model, "response vector" labels were generated from the training data, characterizing the lumen region and lumen center. The response vector serves as a weight profile for computing an error gradient that measures a degree of misalignment of the center of the ROI window from the lumen center. The response vector is generated based on visual inspection and manual annotation of the approximate position of lumen center in a few A-mode or M-mode ultrasound frames. Precision noise in the approximate annotations is easily) averaged out during model training. The lumen center Lumen, is identified as the middle point of the hypoechogenic area of the A-mode signal and it is defined as:

$$\text{Lumen}_c = (P_{Ante} + P_{Post})/2,$$

where $P_{Ante}$ is a position of the first wall portion, anterior artery wall, and $P_{Post}$ is a position of the second wall portion, posterior artery wall, wherein the walls are positioned at depths where the signal peaks laterally from the lumen center.

Further, two cut-off points are set in the response vector halfway between the lumen center and the posterior and anterior walls. Thus an anterior cut-off point $P_{cut\text{-}off(a)}$ and a posterior cut-off point $P_{cut\text{-}off(p)}$ may be set and defined as:

$$P_{cut-off(a)} = (\text{Lumen}_c + P_{Ante})/2,$$

$$P_{cut-off(p)} = (\text{Lumen}_c + P_{Post})/2.$$

Within the cut-off region between the cut-off points, a squared Euclidean distance $d_i$ of a point i at depth $p_i$ towards the lumen center can be computed as:

$$d_i = (p_i - Lumen_c)^2,\ P_{cut-off(a)} < i < P_{cut-off(p)}.$$

These distance values may be normalized in a range [0-1] and may then be used to set the values of the response vector $R_i$ as $$R_i = \begin{cases} 1 - \dfrac{d_i}{(\text{Lumen}_c - P_{cut-off})^2}, & |P_{cut-off(a)} < i < P_{cut-off(p)} \\ 0, & |\text{Other} \end{cases}.$$

During training, misalignment of the window of the region of interest around the lumen center may be penalized by comparing a midpoint position of the response vector (i.e., the lumen center) with a midpoint of the window of the region of interest, and measuring a distance between the two midpoints, e.g., by means of a regression metric such as mean square error (MSE). This may be particularly suitable if a fully connected layer is used instead of the average pooling layer described above.

However, using the average pooling layer 306, which is parameterless (in order to enable training the model with less training data without fear of overfitting), the misalignment may instead be measured and more effectively corrected by computing a total pointwise residual error (MSE) between the response vector and the output of the second convolution layer. Then, this total pointwise residual error may be used for directly applying updates to the parameters of the two convolution layers 302, 304.

In an embodiment, the ROI machine learning model may be implemented with features set forth in Table 1.

TABLE 1

Settings of ROI machine learning model

| Setting | Type or Value |
|---|---|
| Activation Function | LeakyReLU |
| Loss Function | MSE |
| Optimizer | Adam |
| Regularization | L2-norm, Dropout |
| Dropout Probability | 0.05 |
| Weight Decay | 1e−4 |

Once the region of interest has been determined, the diameter of the artery may be determined based on analysis of the region of interest of the ultrasound data.

The diameter of the artery may be determined based on the pre-processed data. For instance, the extracted envelope of the ultrasound response within the region of interest may be used for determining the diameter of the artery.

The diameter of the artery may be determined by a digital signal processing algorithm, which may be configured to determine the first and second walls within the region of interest and further to determine the distance therebetween for determining the diameter of the artery.

However, according to an embodiment, the diameter of the artery is determined using a machine learning model. The machine learning model for determining the diameter of the artery is referred to herein as a cross-sectional width (CSW) machine learning model.

Given a region of interest that includes the artery walls, the CSW machine learning model is trained to calculate an estimate of the diameter of the artery to enable tracking the diameter during heartbeat. Since the diameter of the artery is to be tracked over time, use of neural network model types including recurrent neural network (RNN) models may be useful. While it is possible to use a neural network model including RNN models, it has been found that using a neural network model, wherein determining the diameter of the artery is performed individually for each set of ultrasound data by the machine learning model, provides better performance, with less training time and data.

Figure 6:
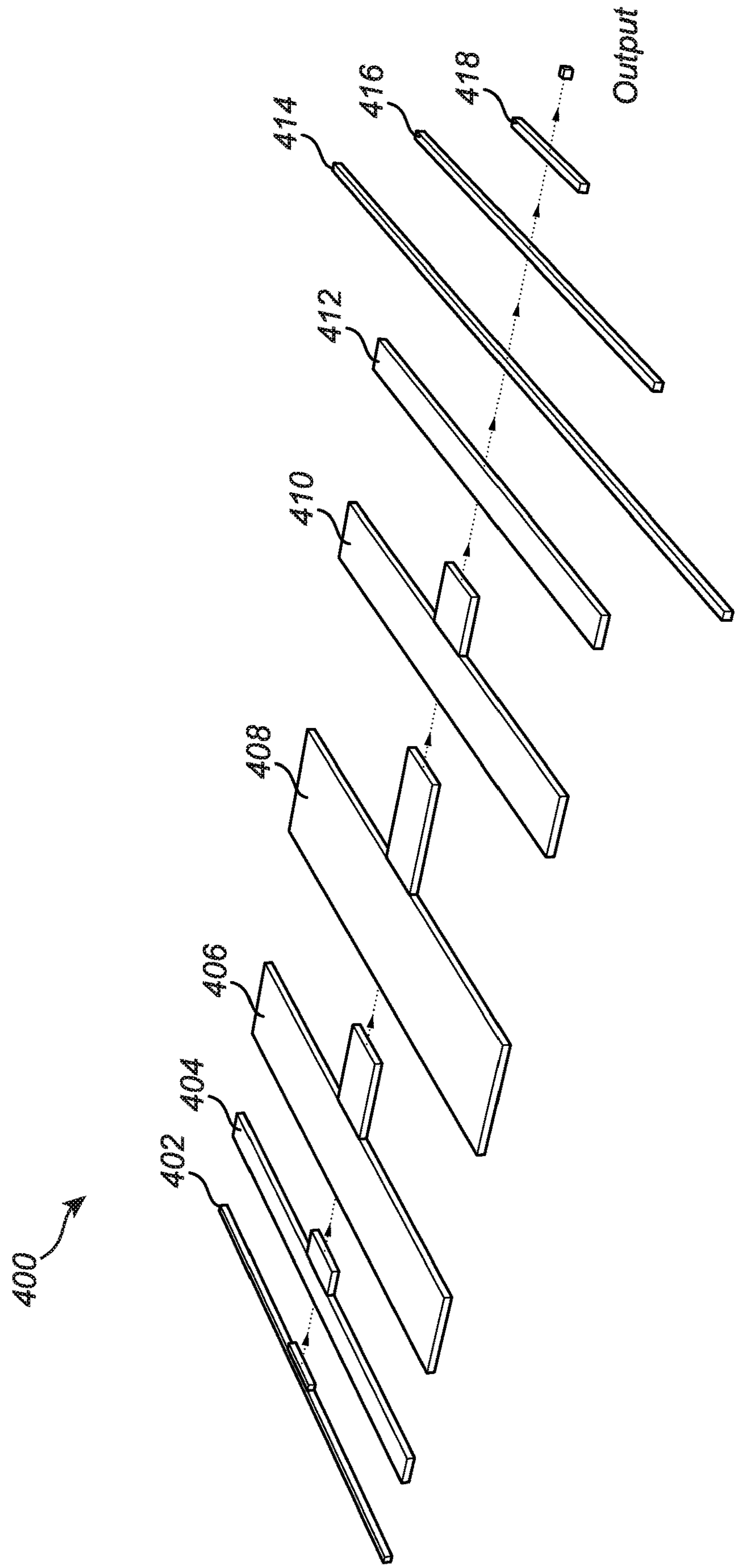
FIG. 6 is a schematic view of a machine learning model for determining the cross-sectional width of the artery.

Referring now to FIG. 6, an embodiment of the CSW machine learning model is shown.

In the embodiment shown in FIG. 6, the CSW machine learning model comprises a neural network architecture 400 having five convolutional layers 402, 404, 406, 408, 410 of similar width, but incrementally increasing in number of channels in the first four convolutional layers 402, 404, 406, 408 and then downsampling the number of channels in the last convolutional layer 410. The convolutional layers are followed by a flatten layer 412 providing a transition between the last convolutional layer 412 to a fully connected layer 414. The CSW machine learning model further comprises a hierarchy of three fully connected layers 414, 416, 418 that gradually combine and summarize convolutional features to compute an estimator of the distension of the artery.

Between convolutional layers 402, 404, 406, 408, 410, batch normalization may be provided. It should further be noted that while up-sampling and then down-sampling across channels is performed, no max-pooling layer for determining a maximum value across layers is used. Such max-pooling layer may distort information about relative positions of the arterial walls, which is needed to estimate the diameter, so max-pooling makes training harder and deteriorates the performance.

The model 400 was trained with Huber loss, instead of more commonly used MSE loss. Huber loss may be beneficially used, because Huber loss may provide robustness in face of the abrupt high-amplitude difference variations of the A-mode signal across depths as the ultrasound pulse enters and exits the lumen region of the artery.

In an embodiment, the CSW machine learning model may be implemented with features set forth in Table 2.

TABLE 2

Settings of CSW machine learning model

| Setting | Type or Value |
|---|---|
| Activation Function | ReLU |
| Loss Function | Huber Loss |
| Optimizer | Adam |
| Regularization | L2-norm, Dropout |
| Dropout Probability | 0.08 |
| Weight Decay | 1e−4 |
| Initialization | Xavier Uniform |
| Normalization | Batchnorm1D |

The method may further comprise applying a smoothing process to a time sequence of determined diameters based on the sets of ultrasound data.

The output of the CSW machine learning model 400 for estimating the artery diameter may not provide a smooth waveform, since the CSW machine learning model 400 determines the diameter at each point in time individually. Therefore, to eliminate high frequency noise, a time sequence of artery diameters output from the CSW machine learning model 400 may be post-processed for smoothing the time sequence. The smoothing process may be provided by using a Savitzky-Golay filter, which is commonly applied to time-series signals to reduce high frequency noise without distorting the signal tendency. The order of the filter may be set as 5, and window size to 31 samples (corresponding to 62 ms if a sampling frequency of 500 Hz is used), hence preserving higher frequency components in the waveform.

As mentioned above, an array of ultrasound transducers may be used for detecting reflection of ultrasound along a plurality of parallel lines. The parallel lines may extend in different cross sections of the artery along a longitudinal direction of the artery.

Thus, the processing unit 120 may be configured to receive a plurality of time sequences corresponding to the parallel lines. These time sequences may be referred to as parallel time sequences and may also be processed in parallel or at least be separately processed to determine the cross-sectional width of the artery in respective cross-sections.

This may allow the cross-sectional width of the artery to be monitored in several locations along extension of the artery.

Additionally or alternatively, the results of the cross-sectional widths from the parallel lines may be combined, which may allow uncertainty to be reduced in monitoring of changes of the cross-sectional width during the time sequence.

The time sequence of sets of ultrasound data may further be processed for identifying a segment in the time sequence corresponding to a cardiac cycle. Changes of the diameter of the artery during a cardiac cycle may be of particular interest for determining a health condition of the subject. Thus, identifying of a segment in received data corresponding to the cardiac cycle may be useful in analyzing health of the subject.

The segment corresponding to the cardiac cycle may be identified using a machine learning model. The machine learning model for determining the segment corresponding to a cardiac cycle (CC) is referred to herein as a CC machine learning model.

Figure 7:
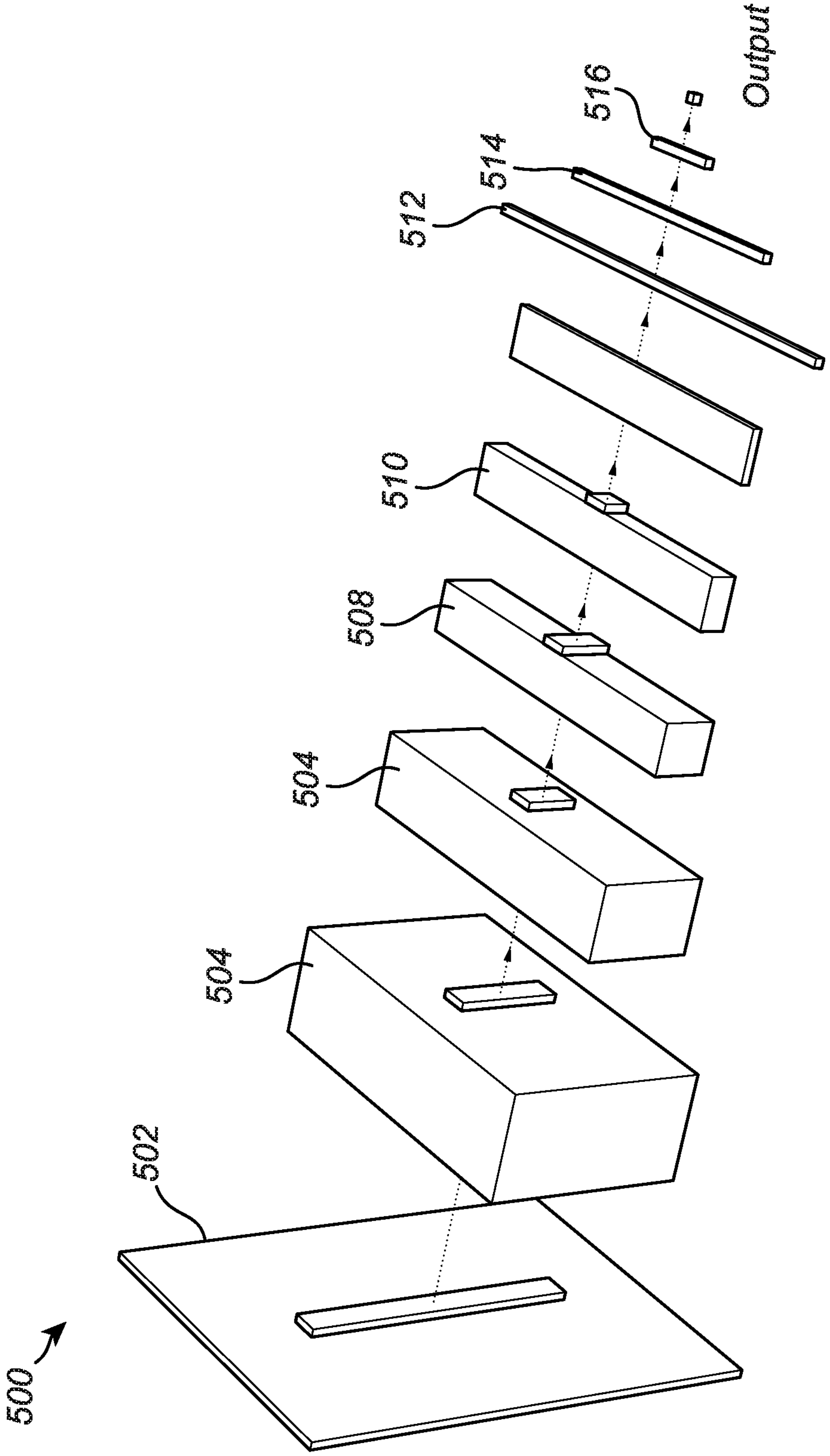
FIG. 7 is a schematic view of a machine learning model for identifying segments in the time sequence of sets of ultrasound data.

Referring now to FIG. 7, an embodiment of the CC machine learning model 500 is shown.

The CC machine learning model may treat the time sequence of sets of ultrasound data as an ultrasound image. The CC machine learning model may receive the ultrasound data in the determined region of interest as input such that the determination of the segments may be performed on cropped data.

The CC machine learning model may use a two-dimensional convolution neural network designed to segment the long ultrasound image into individual heart cycles, based on CC markers. In order to solve this problem in the image perspective, the data format fed into the neural network should be images, containing a window of time samples at a given time point. Thus, sliding window of a certain length is set as the input of the neural network.

The input size of the sliding windows is set to 500*300 (depth*time), which can include the full range of movements of the artery walls. The sliding window may thus comprise almost one heart cycle to include as many temporal features as possible, while keeping only one CC marker in the current frame at most.

The CC machine learning model 500 may use non-square, large-sized kernels to integrate the information on the depth axis and compress it into a sequence similar to a time series. In the choice of specific size for the depth and the time dimension, it is decided that the size in depth dimension should cover at least half of the diameter of the lumen plus the width of the artery. A few convolution operations 502, 504, 506, 508, 510 in the depth dimension are able to compress the ultrasound image into a sequence with only a few variables for every time sample. For the time dimension, the kernel size is expected to include the regional movement of the artery (to be able to identify whether the artery wall is going inwards or outwards), while after the convolution layers, the resulting sequence is similar in the length of the original time samples.

In this way, the features in the images are extracted by the convolution layers into a time series efficiently without sequential processing of data in time and depth dimension. To make the neural network shift-sensitive to allow a regional feature to shift in consecutive windows, max-pooling is not applied after each convolution layer to preserve the location property of the extracted features. Hence, the compression (downsampling) of the image data into a feature map is only achieved by the large kernels without padding. In this way, the feature map after each convolution layer is expected to decrease in size.

To properly design the label for the CC markers, it is decided that a distance metric is a good representation related to the probability of the occurrence of the CC marker. Starting from the first frame of one window, the label is set to be the distance to the nearest ECG marker. To have more continuous and a large range, the label is chosen to be L1-norm distance, without normalization to 0-1 range because of the maximum distance is not constant in different positions on time dimension.

Apart from the regression of L1-norm distance, a classification scheme of quantized distance of the starting frame and the succeeding ECG marker is also designed. It turns out that the regression scheme has a better accuracy since the quantization is downsampling the time samples and quantized distance in classification only relates ECG marker and current frame in one direction. After the convolution layers, fully connected layers 512, 514, 516 are applied to readout the output of the feature maps. Depending on the label, the number of output neurons on the last layer can be altered (1 output neuron for regression, number of classes for classification).

In an embodiment, the CC machine learning model may be implemented with features set forth in Table 3.

TABLE 3

Settings of CC machine learning model

| Setting | Type or Value |
|---|---|
| Activation Function | ReLU |
| Loss Function | MSE |
| Optimizer | Adam |
| Regularization | L2-norm |
| Weight Decay | 1e−4 |
| Initialization | Xavier Uniform |

The determined diameter of the artery may be used for monitoring a health condition of the subject. In this regard, thanks to determining the diameter of the artery, a biomedical marker may be determined to provide an indication or representation of cardiovascular health.

In particular, the biomedical marker may be determined based on determined information of how the diameter of the artery changes in the time sequence. For instance, the biomedical marker may be determined based on analysis of a magnitude of the changes of the diameter within the time sequence, such as comparing a minimum diameter and a maximum diameter during a cardiac cycle.

The biomedical marker may also or alternatively be determined based on determining a particular point in time within the time sequence, such as a point in time at which the artery has a maximum diameter or a minimum diameter. This point in time may be used as a marker of a particular feature of the cardiac cycle, which may be used for defining a pulse arrival time at the artery.

For instance, the time sequence of the diameter of the artery may be analyzed for finding a point in time corresponding to a maximum slope in the time sequence of the artery diameter. This may be a feature which is easily and robustly extracted from the time sequence and may hence be useful for further analysis or as a direct representation as a biomedical marker.

The biomedical marker may thus be determined by computing a value representing the biomedical marker based on the determined diameter of the artery in the time sequence. The computation to be performed will depend on the type of biomedical marker to be determined.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A method for determining a cross-sectional width of an artery, said method comprising:

receiving a time sequence of sets of ultrasound data, each set representing reflection of ultrasound along a line extending through tissue including the artery at a single point in time in the time sequence; and for each set of ultrasound data:

determining, using a machine learning model, a region of interest within the ultrasound data, wherein the region of interest is determined using one or more kernels being compared to the ultrasound data, wherein each kernel represents a first wall portion at a first side of a cross-section of the artery, a second wall portion at a second side of the cross-section of the artery, and a lumen between the first and the second wall portions;

determining the cross-sectional width of the artery based on analysis of the region of interest of the ultrasound data; and pre-processing each set of ultrasound data to form a univariate representation of an ultrasound response from the tissue including the artery.

2. The method according to claim 1, wherein the pre-processing comprises extracting an envelope of the ultrasound response using a Hilbert transform and computing a magnitude of the envelope.

3. The method according to claim 1, wherein the determining of the cross-sectional width is based on the univariate representation of the ultrasound response in the region of interest.

4. The method according to claim 1, wherein determining the cross-sectional width of the artery is performed using a cross-sectional width machine learning model which is configured to receive the region of interest of the ultrasound data.

5. The method according to claim 4, wherein determining the cross-sectional width of the artery is performed individually for each set of ultrasound data by the cross-sectional width machine learning model.

6. The method according to claim 5, further comprising applying a smoothing process to a time sequence of determined cross-sectional widths based on the sets of ultrasound data.

7. The method according to claim 1, wherein the one or more kernels comprise a plurality of convolution kernels, wherein each convolution kernel corresponds to a respective size of the artery and represent values in the ultrasound data forming two peaks of high values separated by low values in between the peaks.

8. The method according to claim 7, wherein the machine learning model for determining the region of interest comprises at least two convolution layers, wherein a first layer uses the plurality of convolution kernels, and a second layer forms an average of output from each of the plurality of convolution kernels in the first layer.

9. The method according to claim 1, further comprising processing the time sequence of sets of ultrasound data using a cardiac cycle machine learning model, for identifying a segment in the time sequence corresponding to a cardiac cycle.

10. The method according to claim 1, wherein the method comprises receiving a plurality of parallel time sequences of sets of ultrasound data representing reflection of ultrasound along parallel lines in different cross sections of the artery along a longitudinal direction of the artery, wherein each of the parallel time sequences is processed to determine the cross-sectional width of the artery in respective cross-sections.

11. A method for determining a biomedical marker, said method comprising the method for determining the cross-sectional width of the artery according to claim 1 and computing a value representing the biomedical marker based on the determined cross-sectional width of the artery in the time sequence.

12. A non-transitory computer program product comprising computer-readable instructions, which, when executed on a processing unit, cause the processing unit to perform the method according to claim 1.

13. A device for determining a cross-sectional width of an artery, said device comprising a processing unit configured to:

receive a time sequence of sets of ultrasound data, each set representing reflection of ultrasound along a line extending through tissue including the artery at a single point in time in the time sequence; and for each set of ultrasound data:

determine, using a machine learning model, a region of interest within the ultrasound data, wherein the region of interest is determined using one or more kernels being compared to the ultrasound data, wherein each kernel represents a first wall portion at a first side of a cross-section of the artery, a second wall portion at a second side of the cross-section of the artery, and a lumen between the first and the second wall portions;

determine the cross-sectional width of the artery based on analysis of the region of interest of the ultrasound data, and pre-process each set of ultrasound data to form a univariate representation of an ultrasound response from the tissue including the artery.

14. The device according to claim 13, further comprising an ultrasound sensor configured to be arranged in relation to the tissue including the artery, to emit ultrasound into the tissue, to detect the time sequence of sets of ultrasound data, and to transfer the time sequence of sets of ultrasound data to the processing unit.

15. A method for determining a cross-sectional width of an artery, said method comprising:

receiving a time sequence of sets of ultrasound data, each set representing reflection of ultrasound along a line extending through tissue including the artery at a single point in time in the time sequence; and for each set of ultrasound data:

determining, using a machine learning model, a region of interest within the ultrasound data, wherein the region of interest is determined using one or more kernels being compared to the ultrasound data, wherein each kernel represents a first wall portion at a first side of a cross-section of the artery, a second wall portion at a second side of the cross-section of the artery, and a lumen between the first and the second wall portions; and determining the cross-sectional width of the artery based on analysis of the region of interest of the ultrasound data, wherein the one or more kernels comprise a plurality of convolution kernels, wherein each convolution kernel corresponds to a respective size of the artery and represent values in the ultrasound data forming two peaks of high values separated by low values in between the peaks.

16. A method for determining a cross-sectional width of an artery, said method comprising:

receiving a time sequence of sets of ultrasound data, each set representing reflection of ultrasound along a line extending through tissue including the artery at a single point in time in the time sequence; and for each set of ultrasound data:

determining, using a machine learning model, a region of interest within the ultrasound data, wherein the region of interest is determined using one or more kernels being compared to the ultrasound data, wherein each kernel represents a first wall portion at a first side of a cross-section of the artery, a second wall portion at a second side of the cross-section of the artery, and a lumen between the first and the second wall portions; and determining the cross-sectional width of the artery based on analysis of the region of interest of the ultrasound data, wherein the method comprises receiving a plurality of parallel time sequences of sets of ultrasound data representing reflection of ultrasound along parallel lines in different cross sections of the artery along a longitudinal direction of the artery, wherein each of the parallel time sequences is processed to determine the cross-sectional width of the artery in respective cross-sections.

* * * * *